(12) United States Patent
Boebel et al.

(10) Patent No.: US 8,128,650 B2
(45) Date of Patent: Mar. 6, 2012

(54) MEDICAL INSTRUMENT

(75) Inventors: Manfred Boebel, Bauschlott (DE);
Stephan Prestel, Rheinstetten-Moersch (DE); Sybille Bruestle, Sternenfels (DE); Ernst Falk, Sternenfels-Diefenbach (DE); Gerhard Fritz Buess, Windach (DE)

(73) Assignee: Richard Wolf GmbH, Knittlingen (DE)

( * ) Notice: Subject to any disclaimer, the term of this patent is extended or adjusted under 35 U.S.C. 154(b) by 357 days.

(21) Appl. No.: 12/407,450

(22) Filed: Mar. 19, 2009

(65) Prior Publication Data
US 2009/0240274 A1 Sep. 24, 2009

(30) Foreign Application Priority Data
Mar. 20, 2008 (DE) .......................... 10 2008 015 418

(51) Int. Cl.
*A61B 17/00* (2006.01)
(52) U.S. Cl. ...................................................... 606/205
(58) Field of Classification Search .................. 600/104, 600/136–139, 141, 142; 606/170, 174, 205–208, 606/210, 211
See application file for complete search history.

(56) References Cited

U.S. PATENT DOCUMENTS

| | | | | |
|---|---|---|---|---|
| 5,201,743 | A * | 4/1993 | Haber et al. | 606/147 |
| 5,520,678 | A | 5/1996 | Heckele et al. | |
| 5,620,415 | A | 4/1997 | Lucey et al. | |
| 5,807,241 | A | 9/1998 | Heimberger | |
| 2002/0095175 | A1* | 7/2002 | Brock et al. | 606/205 |
| 2003/0236549 | A1 | 12/2003 | Bonadio et al. | |
| 2004/0098040 | A1* | 5/2004 | Taniguchi et al. | 606/205 |
| 2005/0096694 | A1 | 5/2005 | Lee | |
| 2007/0276430 | A1 | 11/2007 | Lee et al. | |
| 2008/0058861 | A1* | 3/2008 | Cooper et al. | 606/205 |

FOREIGN PATENT DOCUMENTS
EP 0 764 423 B1 9/2004
GB 2284242 A 5/1995

* cited by examiner

*Primary Examiner* — Ryan Severson
(74) *Attorney, Agent, or Firm* — Panitch Schwarze Belisario & Nadel LLP

(57) ABSTRACT

A medical instrument has a handle arranged at the proximal end, a shank extending distally proceeding from the handle, and a movable jaw part arranged at the distal end of the shank. The shank is designed to be rigid and includes at least one proximal bend region and at least one distal bend region, in which the extension direction of the shank changes. A section of the shank in which the distal bend region is situated may be rotated about the longitudinal axis relative to a section of the shank in which the proximal bend region is situated. The jaw part is rotatable relative to the shank about its distal longitudinal axis at the distal end.

20 Claims, 9 Drawing Sheets

MEDICAL INSTRUMENT

BACKGROUND OF THE INVENTION

The invention relates to a medical instrument, in particular to a medical instrument for translumenal, endoscopic surgery via natural body openings.

For example, with endoscopic operations in the abdomen, a relatively narrow-lumen, long access tube must be used via transvaginal access. It is because of this narrow-lumen access tube that it is difficult at the location of the operation, for example the gall bladder, to create the necessary free spaces for retraction, preparation, dissection and coagulation. This is made additionally difficult due to the fact that the optical system and the instruments all come from the same direction. A further problem is the fact that the handling of the individual instruments mutually inhibits one another.

BRIEF SUMMARY OF THE INVENTION

It is therefore the object of the invention to create a medical instrument which, with translumenal endoscopic surgery via natural body openings, on the one hand creates improved operational possibilities and on the other hand permits the application of several instruments without the handling of the instruments being mutually handicapped.

This object is achieved by a medical instrument comprising a handle arranged at a proximal end, a shank extending distally proceeding from the handle, and a movable jaw part arranged at a distal end of the shank, wherein the shank is designed to be rigid and comprises at least one proximal bend region and at least one distal bend region, in which an extension direction of the shank changes. A section of the shank, in which the distal bend region is situated, is rotatable about a longitudinal axis relative to a section of the shank in which the proximal bend region is situated. The jaw part is rotatable relative to the shank about its distal longitudinal axis at the distal end.

The medical instrument according to the invention comprises in a known manner a handle at its proximal end. A shank extends distally from this handle, and a movable jaw part, for example for cutting or gripping, is arranged on the distal end of this shank. The shank is preferably designed very long, in order to permit the application of the instrument through a long and narrow-lumen access tube, for example a tube which is more than 400 mm long. The shank must be longer than the tube for this.

According to an embodiment of the invention the shank is rigid, i.e., it is not designed to be flexible in a direction transverse to its longitudinal axis. This, in a very simple manner, permits a precise positioning of the shank. At least two bend regions are formed in the shank, in which the extension direction of the shank changes. That is, the shank is bent or kinked in these bend regions, so that the longitudinal axes of the shank sections bordering the bend region run at an angle to one another. Here, one preferably selects an angle between 5 and 30 degrees. Thus, due to the rigid design of the shank, it is a case of a set, predetermined kink angle or bend angle of the shank in the bend regions. Of the two bend regions, one is situated in the proximal region of the shank and the second in the distal region of the shank, wherein the shank preferably extends in a straight manner between the two bend regions. Thereby, the shank further preferably extends with the greatest part of its length between the two bend regions. This straight section between the two bend regions is that section which runs through the access tube during the operation. The two bend regions are then situated in each case outside the access tube, one at the distal side and one at the proximal side of the access tube. It is to be understood that both bend regions may have the same bend angle or kink angle, but may also have different bend angles or kink angles.

According to an embodiment of the invention, furthermore, one section of the shank, in which the distal bend region is situated, is rotatable about the longitudinal axis of the shank relative to a section of the shank in which the proximal bend region is situated. The distal end of the shank may be rotated or pivoted transversely to the longitudinal axis of an access tube or transversely to the extension direction of the shank between the bend regions by way of this rotation ability. In this manner, greater free spaces are created in the operating region compared to the application of instruments which extend in a straight manner. Thus, with the application of two such instruments, their distal ends or the jaw parts which are arranged there may be moved apart or moved toward one another by way of a corresponding rotation of the two distal ends of the instruments. Thus, for example, with an instrument which is formed as a gripping forceps, the gall bladder may be held and pivoted out of the operation field by rotation of the shank section with the proximal bend region, so that a desired access to the gall bladder is created. Another instrument which is formed as a cutting instrument may then be brought into an optimal cutting position by rotating its section with the proximal bend region. The changing operating situation may thereby render a post-adjustment of the access tube and of the instruments necessary.

Furthermore, according to an embodiment of the invention, the jaw part is rotatable relative to the shank about the longitudinal axis of the shank at its distal end. In this way, the jaw part with its opening maybe brought into the desired angular position in order to grip or cut tissue. The jaw part thereby rotates about the longitudinal axis of the shank section which extends further distally from the distal bend region. This section is preferably designed to be straight, but may also have a further curvature.

By way of the proximal bend region, one succeeds in the handle being bent with respect to the main extension direction of the shank, i.e., the extension direction between the two bend regions. This, with the application of several instruments, permits their handles to be able to extend in one and the same access tube at the proximal side of the access tube in different directions, so that the actuation of the individual handles is not inhibited.

The shank preferably comprises an outer shank tube and the at least one distal bend region is preferably defined by an angle or bend in the outer shank tube. That is, the outer shank tube is angled or bent in the bend region, such that the sections of the shank tube which are situated at the two sides of the bend region extend angled to one another. These sections are preferably in each case designed to be straight. The outer shank tube is designed to be rigid in this bend region, so that a fixed angle or a fixed curvature is given.

The outer shank tube is preferably rotatable relative to a proximal section of the shank. This rotation is effected about the longitudinal axis of the shank section between the two bend regions which preferably extends in a straight manner. Due to this rotation, the distal end of the shank is moved on a circular path which is radially spaced from the rotation axis. In this manner, the distal end with the jaw part may be displaced in its position in a direction transverse to the main extension direction of the shank, i.e., the extension direction between the two bend regions. The longitudinal axis between the bend regions, during the operation, extends essentially parallel to the longitudinal axis of the access tube, since this is the section of the shank which is situated in the access tube.

Moreover, the shank preferably comprises a rigid outer tube which borders the handle, extends only over a proximal bend region of the shank, peripherally surrounds the outer shank tube to the outside, and defines the at least one proximal bend region by an angle or a bend in the outer tube. That is, the rigid outer tube is angled or bent, and this forms the proximal bend region with a fixed bend angle or kink angle. Thus, the two sections of the outer tube which border the bend region extend with their longitudinal axes at an angle to one another. These sections of the outer tube are preferably designed to be straight. The outer tube extends in the proximal direction from the bend region up to the handle and is connected to this. The outer tube extends so far in the distal direction that it ends in the shank section between the bend regions. Preferably, the outer tube extends in the distal direction only slightly beyond the proximal bend region compared to the total length of the shaft.

The outer shank tube is preferably rotatable relative to the outer tube about its longitudinal axis. Two sections of the shank which are rotatable relative to one another are created in this manner. The one section is the section with the proximal bend region and which is defined by the outer tube, and the second section is the section with the distal bend region and which is defined by the outer shank tube.

For rotating the outer shank tube, this is preferably connected at the proximal end to a rotation device in the handle. This may be, for example, a rotation wheel, with which the outer shank tube may be rotated about its rotation axis.

The outer shank tube is preferably designed to be flexible in the proximal bend region, in order to be able to transmit this rotational movement from the handle beyond the first bend region. For this purpose, the shank tube in this region may, for example, be formed of several rigid tube sections which are movably connected to one another. A suitable shank of tube sections which are connected to one another in a movable manner is known for example from European Patent EP 0 764 423 B1. Such a flexibly designed shank may also be rotated in the bend region in the inside of the outer tube, about its longitudinal axis. The outer shank tube, in the distal section behind the bend region, is then designed to be rigid, i.e., non-bendable. Thereby, the rigid outer tube and the rigid section of the outer shank tube overlap over a certain length, in order to create a stable guide for the outer shank tube in the outer tube. The outer shank tube is preferably guided or mounted on the inner periphery of the outer tube. In particular, the bearing region between the rigid part of the outer shank tube and the outer tube may be selected to be so long that transverse forces, which act on the outer shank tube, may be transmitted securely onto the rigid outer tube. The outer shank tube distally of the distal end of the outer tube forms the component giving the shank its stability and bending strength.

Further preferably, the jaw part is rotatably attached at the distal end of the outer shank tube, and a rotatable inner tube is arranged in the outer shank tube. This inner tube is connected at its proximal end to a rotation device in the handle and at the distal end to the jaw part in a rotationally fixed manner. The jaw part via this inner shank may be rotated about its longitudinal axis as described above. For this purpose, the rotation device which is formed, for example, as a rotation wheel is rotated. With this, the inner tube rotates about its longitudinal axis concentrically to the surrounding outer shank tube and to the outer tube. The jaw part then rotates together with the inner shank on account of the rotationally fixed connection between the jaw part and inner shank.

The rotation wheel for the inner shank and a rotation wheel for the outer shank tube are preferably arranged in the handle such that they may be rotated about the same rotation axis and are only spaced axially from one another. Thus, the two hand wheels are gripped simultaneously and rotated differently, so that on rotation of the outer shank tube, the jaw part may be rotated at the same time, wherein the rotation angle and rotation direction of the two elements are independent of one another.

The inner tube is usefully designed flexibly at least in the bend regions. This may, for example, be created by the inner tube in these regions being formed of several rigid tube sections which are movably connected to one another, as is known from EP 0 764 423 B1. By way of this flexibility, i.e., a movability transverse to the longitudinal direction of the inner tube, one ensures that the inner tube may be rotated over the whole length about its longitudinal axis, through the bend regions. That is, the inner tube rotates in all regions of the shank about its longitudinal axis concentrically to the surrounding outer shank tube. Preferably, the inner tube is also designed to be rigid in the axial sections of the inner tube, in which the surrounding outer shank tube extends in a straight manner, since in this way, a low-friction movement of the inner tube is possible and one may give the shank a greater stability. Moreover, in these regions, one may make do without the machining for a design of the sections movable relative to one another, which saves costs.

The design of the inner tube according to the system known from EP 0 764 423 B1 is particularly suitable if sections of the inner tube are not to be designed to be flexible, as previously described. According to the method known from EP 0 764 423 B1, it is specifically very easily possible to only design individual sections of a tube to be flexible, by incorporating the respective separating gaps therein. The same applies to the design of the outer shank tube. Here too, the method known from EP 0 764 423 B1 is suitable, since the separating gaps necessary for the movability only need to be incorporated in an easy manner into one axial section of the shank tube, specifically in the section which extends through the bend region.

Further preferably, an actuation rod for actuating the jaw part extends in the inside of the shank from the handle to the jaw part. This actuation rod extends through the inside of the inner tube from the proximal to the distal end of the shank. The actuation of the jaw part is effected preferably by axial displacement of the actuation rod along the longitudinal axis of the shank. Thereby, depending on the design of the instrument, the jaw part, for example, may be opened by pulling the actuation rod in the proximal direction. Alternatively, it is also possible to provide for a reverse movement, with which the jaw part is closed by pulling the actuation rod in the distal direction. This in particular depends on which one requires the larger actuation force. If the larger force is required for closing the jaw part, then it makes sense for this purpose to pull the actuation rod in the proximal direction. In order for the actuation rod to be able to run through the bend regions, it is likewise useful for the rod to be flexible, but it must have a sufficient strength in order to be able to transmit the required pushing and/or pulling force in the axial direction.

According to a further preferred embodiment, the jaw part is releasably connected to the outer shank tube. This may be useful for cleaning or for the exchange of the jaw part. The releasable connection may, for example, be created by a thread engagement or by a bayonet closure. The jaw part, in the axial direction, advantageously comprises two sections which may be rotated relative to one another. The fixed section located on the proximal side may be releasably connected to the distal end of the outer shank tube via a connection, for example a thread or a bayonet. Thereby, a rotationally secure connection is created. Simultaneously, by suitable means, the distal end of the inner tube usefully comes into non-positive fit or positive fit engagement with the rotatable section of the jaw part, so that a rotationally fixed connection is created between the two. For this purpose, suitable engagement elements and/or catches may be provided on the rotatable distal section of the jaw part and/or on the distal end of the inner tube.

The actuation rod on the distal side is preferably fixedly connected to the jaw part, i.e., in particular to the mechanics for opening and closure, which are situated in the distal rotatable section of the jaw part. If the jaw part is removed from the outer shank tube, then with this design, the actuation rod may thereby be pulled out of the inner tube in the distal direction.

According to a further preferred embodiment, the shank is releasably connected to the handle. This connection is preferably designed as is described in German Patent DE 103 57 105 B3. The releasable connection is thereby preferably designed such that the outer tube, outer shank tube, inner tube, and actuation rod may be separated from the handle. The separation is preferably effected automatically in one working step, i.e., the individual elements do not need to be separated from one another in a manual and individual manner. Vice versa, the connection is designed such that the parts come into engagement with another in the desired manner on assembly. In particular for this purpose, connection elements are provided in the handle, which create a rotationally fixed connection between the outer shank tube and the associated hand wheel, and between the inner tube and the associated hand wheel in the grip part when the shank is connected to the grip part.

According to a particular embodiment, the instrument may be designed as an HF-instrument. For this, the outer shank tube may be insulated to the outside and a connection for a high-frequency voltage supply may be provided on the handle. Preferably, the instrument is thereby designed to be unipolar. Basically, however, a bipolar design is also conceivable, wherein thereby, for example, the outer shank tube and the inner tube and/or the actuation rod may assume the function of the two required electrical leads. The elements must then be suitably insulated with respect to one another.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings.

DETAILED DESCRIPTION OF THE INVENTION

Figure 1:
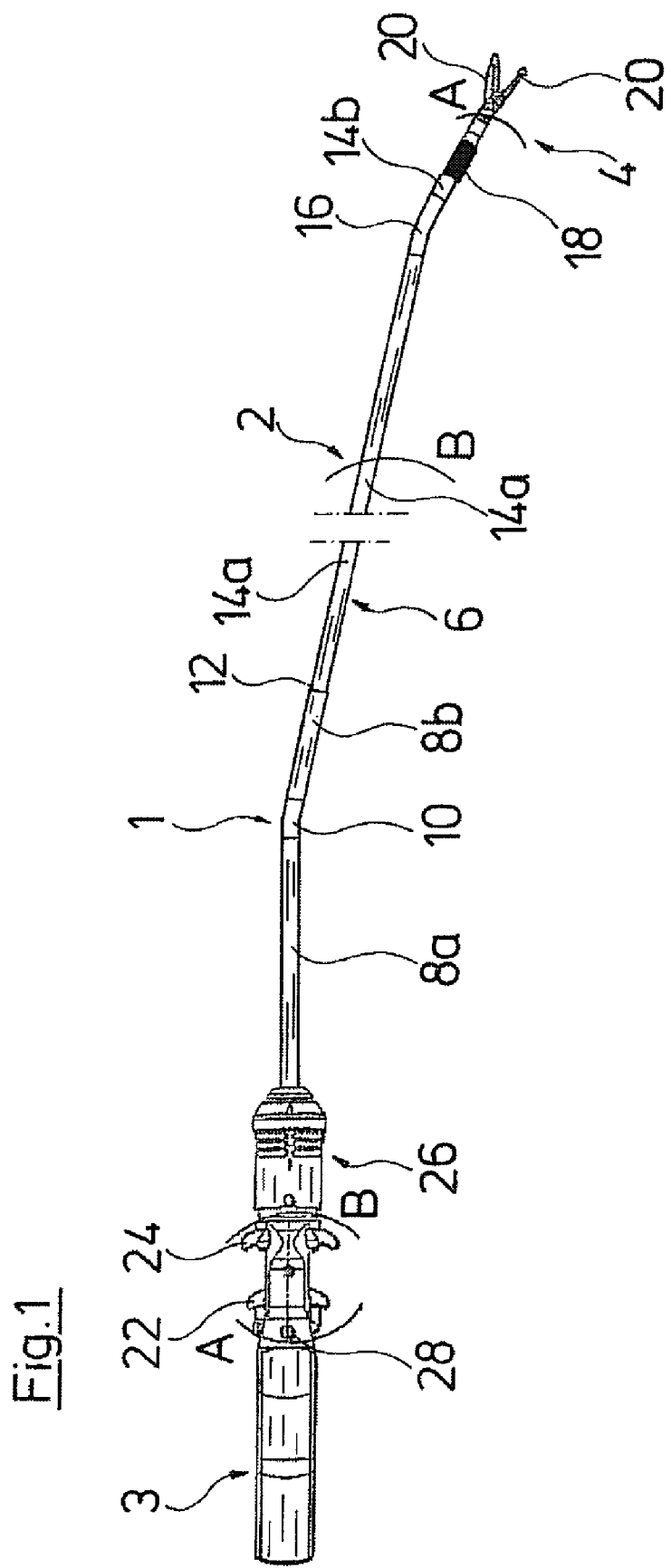
FIG. 1 is a schematic overall view of a medical instrument according to a first embodiment of the invention.
Figure 2:
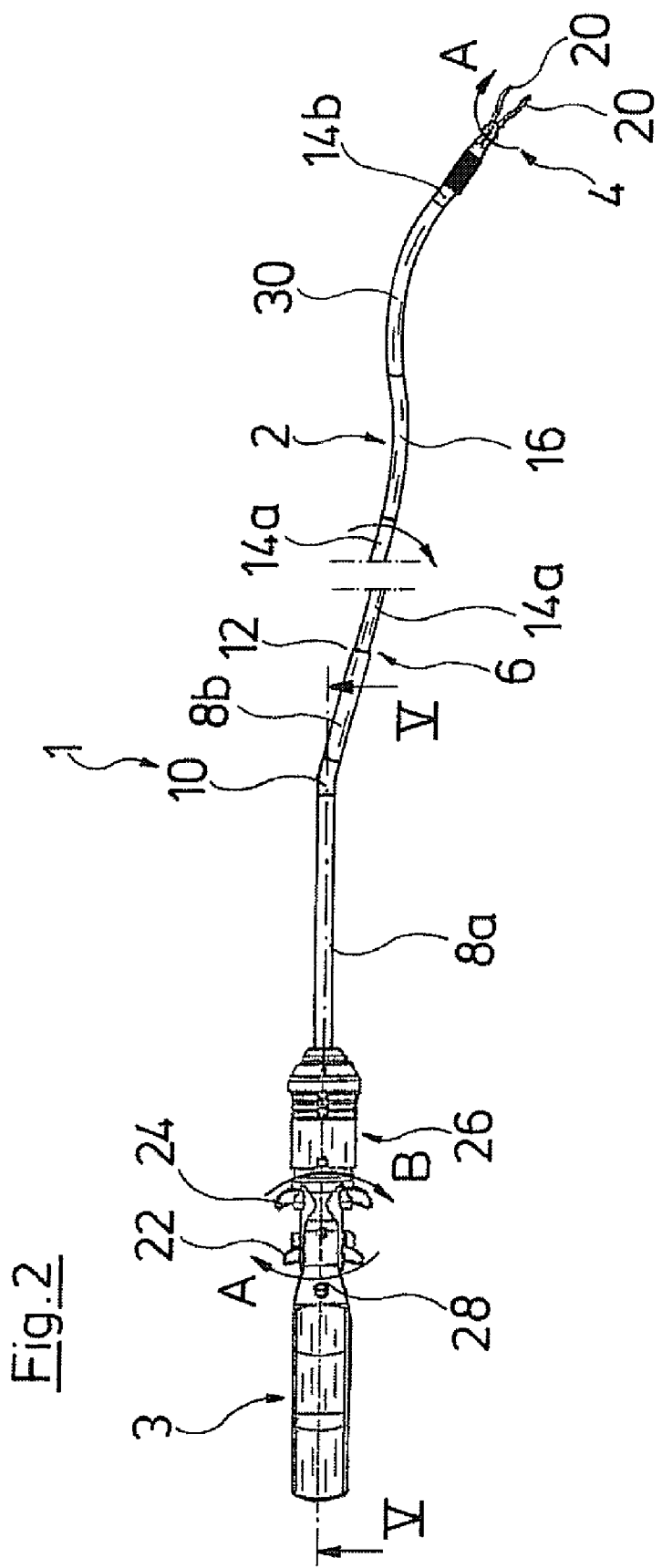
FIG. 2 is a schematic overall view of a medical instrument according to a second embodiment of the invention.

In both shown exemplary embodiments of the invention, i.e. the first embodiment according to FIG. 1 and the second embodiment according to FIG. 2, the instrument 1 consists basically of two parts, specifically a forceps insert 2 and a handle part 3. A jaw part 4 is formed at the distal end of the forceps insert 2. A shank 6, proceeding from the handle part 3, extends in the distal direction to the jaw part 4.

This shank 6 is formed of several parts. First, a rigid outer tube 8 connects directly to the handle 3 in the distal direction, and is formed of two sections 8a and 8b, which are angled to one another and which are firmly connected to one another via a bend region 10. The section 8a and the section 8b as well as the bend region 10 are preferably formed of one part or one piece. The bend region 10 sets a defined angle of the longitudinal axes of the sections 8a and 8b to one another, on account of the rigid design of the outer tube. An outer shank tube 14, which is likewise formed of two sections 14a and 14b which are firmly connected to one another via a rigid bend region 16, extends from the outer tube 8 at the distal end 12. The sections 14a and 14b are thereby formed as one part or as one piece with the bend region 16. A defined angle between the longitudinal axes of the sections 14a and 14b to one another is set by way of the defined angle of the bend region 16, due to the rigid design of the outer shank tube 14.

Thus, as a whole, the shank is angled twice, specifically in the bend region 10 and the bend region 16. The section 14a of the outer shank tube 14 forms the longest section of the shank 6 and is that section which, during the operation, is situated in the inside of an access tube. The bend region 10 with this positioning is situated on the proximal side of the access tube, while the bend region 16 is situated on the distal side of the access tube. The jaw part 4, by way of the threaded sleeve 18 of the jaw part, is connected to the outer shank tube 14 at the distal end of the section 14b. One may also provide a bayonet closure instead of a threaded sleeve. A distal section of the jaw part 4, which is formed essentially by the two parts 20 which are movable relative to one another, is rotatable relative to this proximal threaded sleeve 18. In the embodiment according to FIG. 1, the moving parts 20 of the jaw part are formed as scissors. This design, and in particular the pivoting movability of the parts 20 relative to one another, may be effected in a known manner. The rotation relative to the proximal threaded sleeve 18 is effected about the longitudinal axis of the section 14b of the outer shank tube 14.

Figure 3:
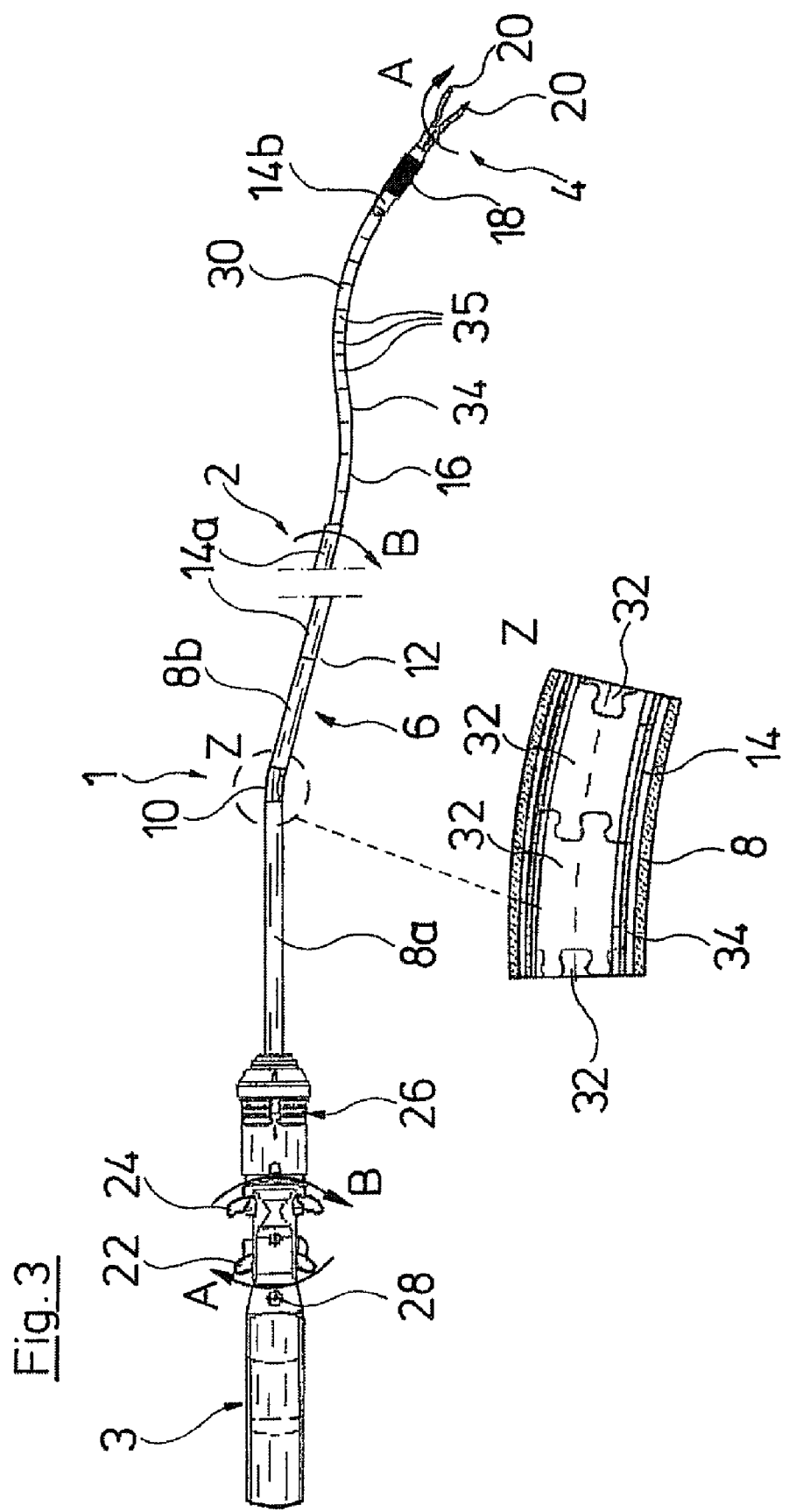
FIG. 3 is another representation of the instrument according to FIG. 2, with a partly sectioned detail view.
Figure 4:
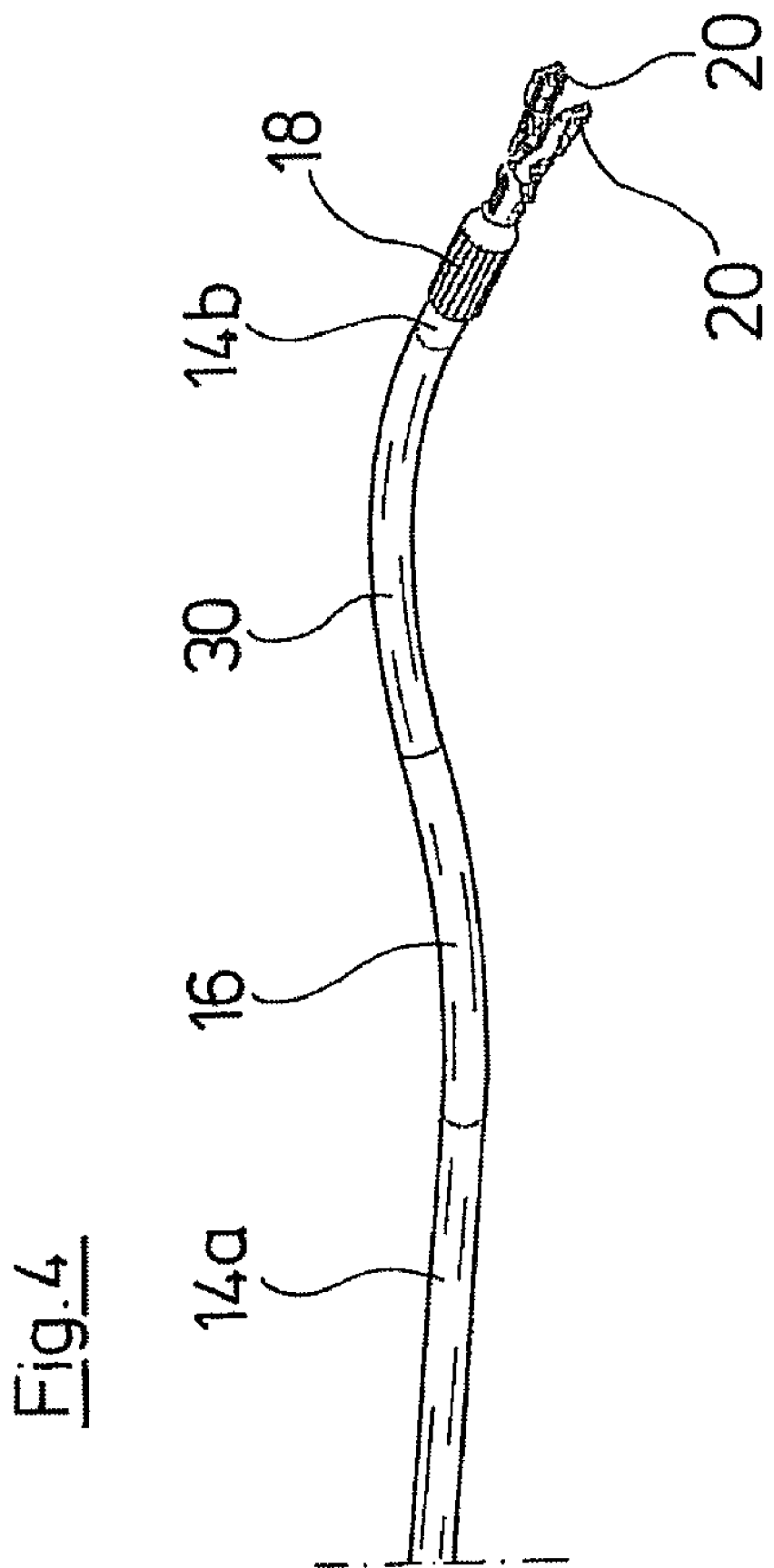
FIG. 4 is a detail view of the distal end of the instrument according to FIG. 2.

Moreover, the outer shank tube 14 is rotatable about the longitudinal axis of the section 14a, relative to the outer tube 8. The rotation of the jaw part 4 and of the outer shank tube 14 is effected by two hand wheels 22 and 24 in the handle part 3. There, the hand wheel 22 is provided for the rotation of the jaw part 4, and the hand wheel 24 for the rotation of the outer shank tube 14. This means that when the hand wheel 22 is rotated in the direction of the arrow A, the jaw part 4 correspondingly rotates in the direction of the arrow A. If the hand wheel 24 is rotated in the direction of the arrow B, then the outer shank tube 14 correspondingly rotates in the direction of the arrow B (FIGS. 1-3).

The forceps insert 2 is releasably connected to the handle part 3 via a coupling 26. This coupling is formed in the manner as is known from German Patent DE 103 57 105 B3. In particular, the coupling 26 ensures that the outer tube 8 is connected to the handle part 3 in a rotationally fixed manner at a certain angle. The coupling 26 moreover ensures a releasable connection of the tubes or shank parts to corresponding components in the handle part 3, the tubes or shank parts being situated in the outer tube 8. Thus, the outer shank tube 14, which extends in the proximal direction through the inside of the outer tube 8, is releasably coupled to the hand wheel 24. Accordingly, an inner tube, which is described later in more detail, is releasably coupled to the hand wheel 22 for rotating the jaw part 4. Moreover, an actuation rod for opening and closure of the moving parts of the jaw part 20 is releasably connected to the grip part of the handle 3.

The handle part, moreover, has an HF-connection 28 for connection to a high-frequency voltage source.

The embodiment according to FIG. 2 differs from the embodiment according to FIG. 1 with regard to two aspects. On the one hand, the moving parts 20 of the jaw part in the embodiment according to FIG. 2 are not formed as scissors, but as gripping forceps. On the other hand, the outer shank tube 14, apart from the bend region 16, comprises a further bend region 30, which connects distally thereto and in which the outer shank tube 14 is bent once again. As a result, the section 14b of the outer shank tube 14, on the one hand, is angled with respect to the section 14a of the outer shank tube 14 and, on the other hand, is offset transversely by a certain amount. A different positioning of the jaw part 4 in the operation field may be achieved in this way.

Now, the inner construction of the shank 6 is explained in more detail by way of FIG. 3, wherein it is to be understood that the inner construction of the shank 6 in the embodiment according to FIG. 1 is identical to the construction shown in FIG. 3. The outer shank tube 14 extends from the handle through the outer tube 8 and extends outwardly at its distal end 12. The outer shank tube 14 is designed to be flexible in the region of the bend region 10, so that the outer shank tube 14 may thereby run through the bend region 10, such that it may be rotated about its longitudinal axis. This is shown in more detail in the cut-out enlargement Z in FIG. 3. As may be recognized, the outer shank tube 14 in this region is formed of several tube sections 32, which are engaged with one another with a positive fit via engagement elements. There, the engagement is such that the individual tube sections 32 are movable relative to one another. This design corresponds in its construction to the bendable tube known from European Patent EP 0 764 423 B1. The method described in this European patent permits the incorporation of suitable separating gaps, which form the tube sections 32 which are movable to one another, into the otherwise rigid outer shank tube 14, only in the bend region 10.

An inner tube 34 is arranged in the inside of the outer shank tube 14, which extends from the distal end of the instrument 1 up to the handle part 3. The inner tube 34 is rotatable in the inside of the outer shank tube 14 about its longitudinal axis. The inner tube 34 is connected at its proximal end to the hand wheel 22. The inner tube 34 at the distal end is connected to the rotatable section of the jaw part 4. If the hand wheel 22 is rotated in the direction of the arrow A, then the inner tube 34 is rotated about its longitudinal axis and transmits this rotational movement to the jaw part 4, so that its distal section is rotated with the moving parts 20 in the direction of the arrow A. In order to be able to angle the bend regions 10, 16 and 30 in a corresponding manner and, despite this, for these to be able to run through in a rotatable manner about the longitudinal axis, the inner tube 34 is designed to be flexible in these regions. The design thereby corresponds to the flexible design of the outer shank tube 14 in the bend region 10. That is, the inner tube 34 is also formed of individual tube sections 35 in the bend or curved sections, and these sections are movably connected to one another, as is known from EP 0 764 423 B1. This design of the inner tube 34 is not shown in detail in the enlargement Z, but it is to be understood that there the inner tube is formed just as in the bend regions 16 and 30.

Figure 5:
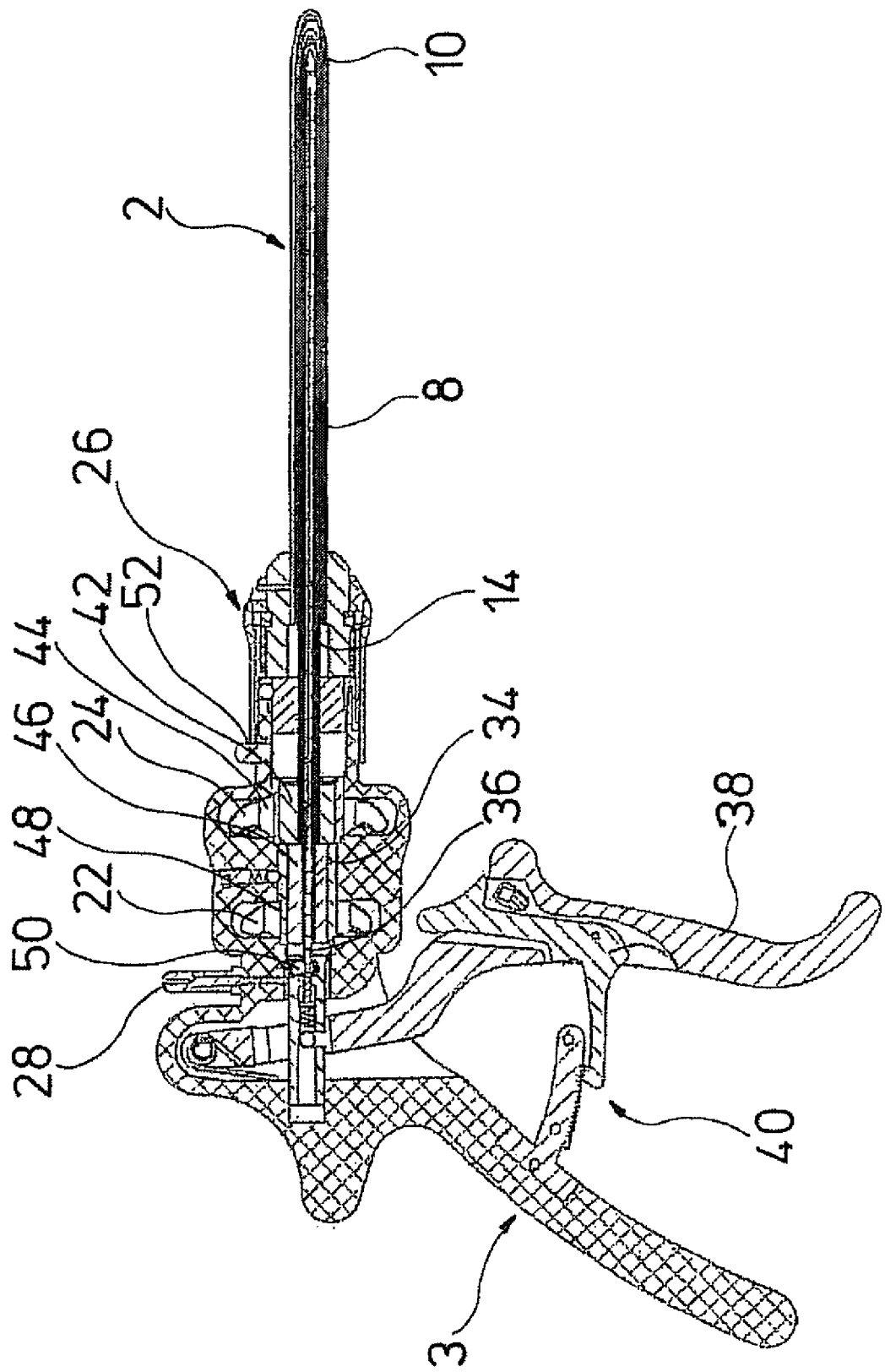
FIG. 5 is a sectioned view of the second embodiment taken along line V-V in FIG. 2.
Figure 6:
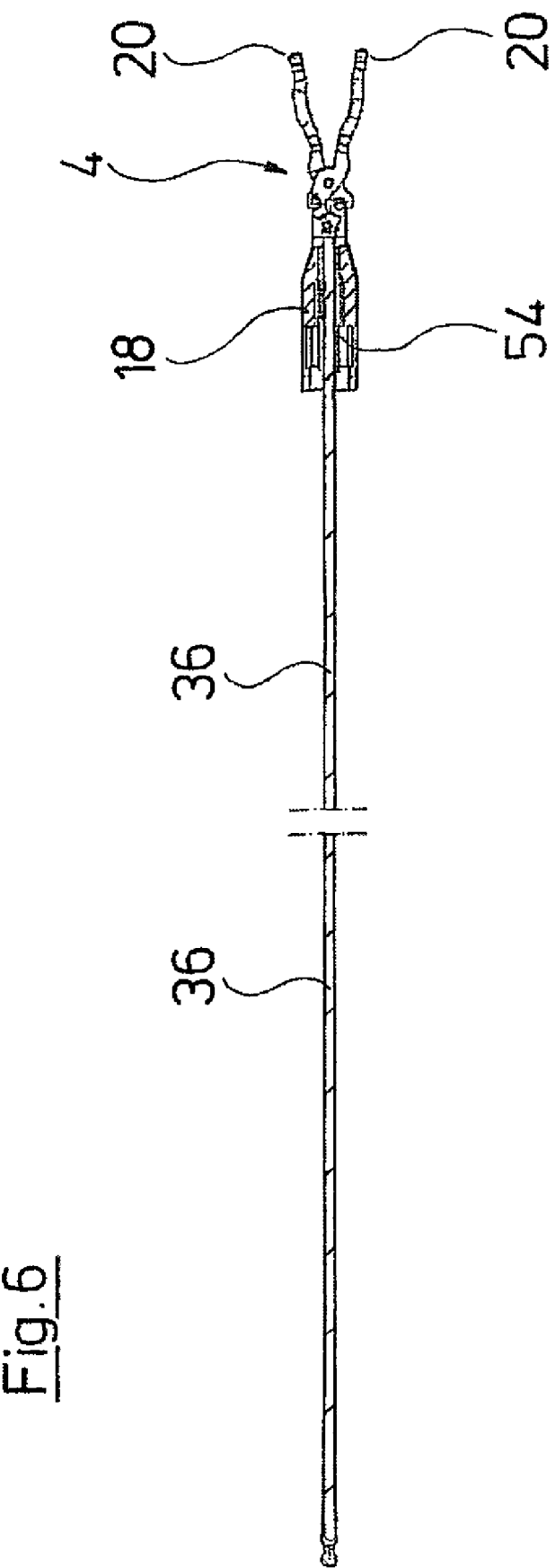
FIG. 6 is an individual view of the jaw part of the medical instruments according to FIGS. 1 to 5.
Figure 7:
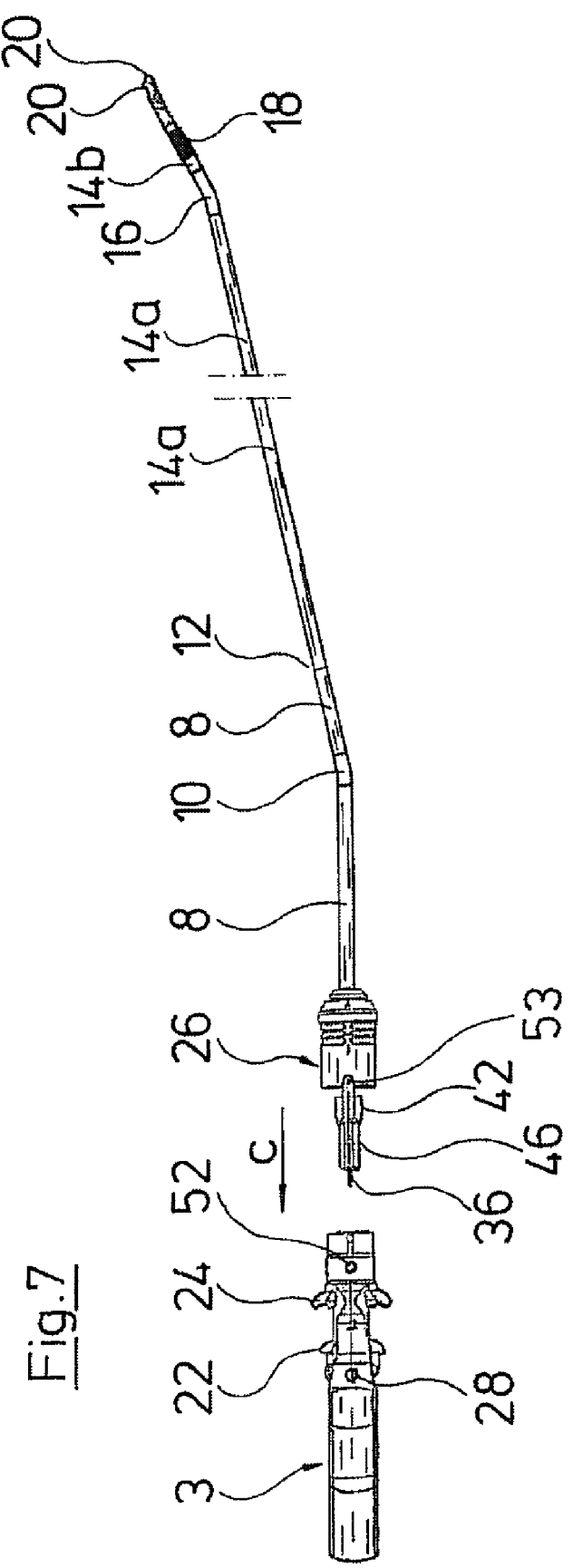
FIG. 7 is another view of the instrument according to FIG. 1, in which the shank is separated from the handle.

As may be recognized in FIGS. 5, 6 and 7, an actuation rod 36 extends through the inside of the inner tube 34 from the handle part 3 to the jaw part 4, by way of whose axial displacement the moving parts 20 of the jaw part may be opened and closed. For this, the proximal end of the actuation rod 36 is connected in the handle part 3 to the moving handle part 38. The moving handle part 38 may be secured in its position via a locking block 40.

As is shown in FIGS. 5 and 7, a spline 42 is arranged at the proximal end of the outer shank tube 14 in a rotationally fixed manner. The spline engages in a corresponding receiver 44 in the hand wheel 24 with a positive fit, in order to transmit a rotational movement of the hand wheel 24 via the spline 42 onto the outer shank tube 14. Accordingly, a spline 46 is arranged on the proximal end of the inner tube 34 in a rotationally fixed manner and engages with a positive fit into a corresponding receiver 48 in the hand wheel 22. Thus, a rotational movement from the hand wheel 22 may be transmitted via the spline 46 onto the inner tube 34.

This connection of the elements permits the coupling part 26 to be put together with the handle part 3 in the direction of the arrow C, wherein the splines 42 and 46 engage with corresponding receivers 44 and 48. Simultaneously, the proximal end of the actuation rod 36 is coupled via a ball lock connection 50 to the moving handle part 38. Otherwise, the coupling 26 is coupled to the handle part 3 in the manner known from DE 103 57 105 B3. Moreover, a rotation locking 52 in the form of a projection is provided on the handle part 3, and this projection engages into a corresponding recess 53 on the coupling 26 and thus connects the outer tube 8 to the handle part 3 in a rotationally fixed manner at a predefined angular position.

Figure 8:
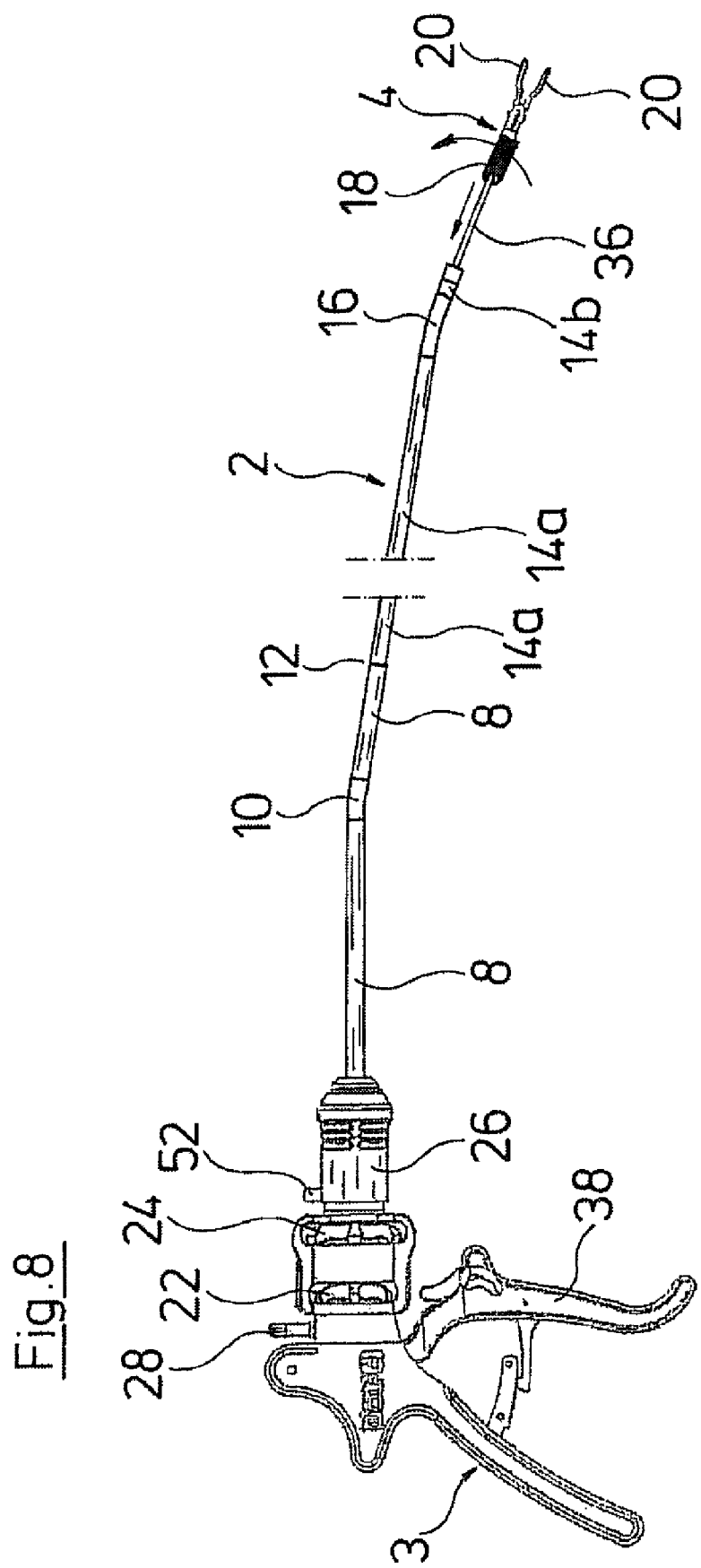
FIG. 8 is another overall view of the instrument according to FIGS. 1 and 7 with a partly removed jaw part which is formed as a gripping forceps.

FIG. 6 shows the removed jaw part 4 on which the actuation rod 36 is connected to the mechanics of the moving parts 20 in a fixed manner on the proximal side. The jaw part 4 may be screwed with the proximal threaded sleeve 18 to the distal end of the outer shank tube 14. Thereby, a coupling part 54 engages with the distal end of the inner tube 34 with a positive fit, so that a rotation of the inner tube 34 is possible via the coupling part 54 onto the distal section of the jaw part 4. The jaw part 4 is shown in the partly removed condition in FIG. 8.

Figure 9:
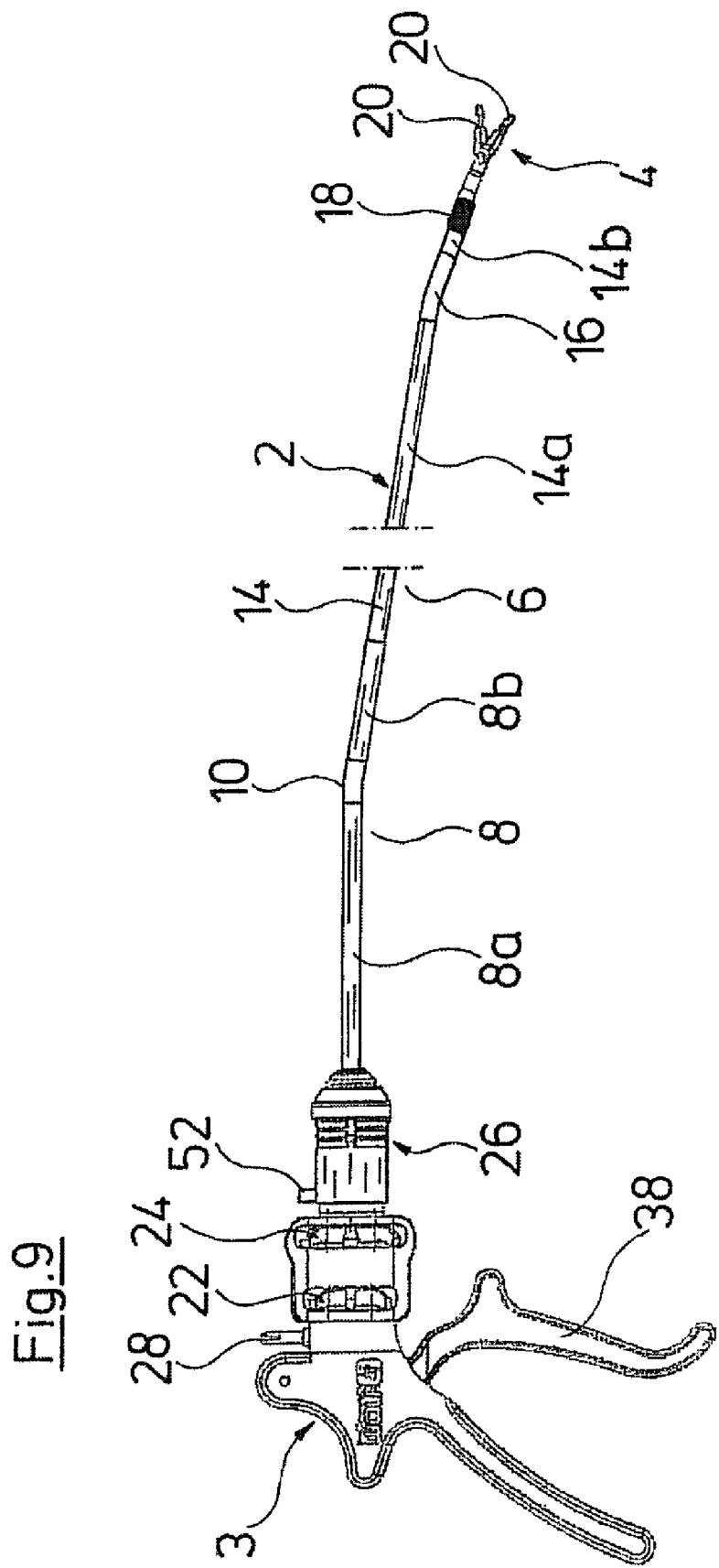
FIG. 9 is another overall view of the instrument according to FIG. 8, wherein the jaw part is formed as a scissors.

FIG. 9 once again shows a lateral view of the instrument according to FIG. 1. It is to be understood that the design of the jaw part 4 may be effected in different manners. Thus, the design may also be as a scissors in the second embodiment according to FIG. 2, or vice versa the design as a gripping forceps with the first embodiment according to FIG. 1. The outer shank tube 14 is insulated to the outside for the use of the instrument as an HF-instrument. The instrument, however, need not necessarily be designed as an HF-instrument. In this case, one may then make do without the insulation as well as the HF-connection 28.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A medical instrument comprising a handle (3) arranged at a proximal end, a shank (6) extending distally proceeding from the handle (3), and a movable jaw part (4) arranged at a distal end of the shank (6), wherein:
    the shank (6) is designed to be rigid and comprises at least one proximal bend region (10) and at least one distal bend region (16, 30), in which an extension direction of the shank (6) changes,
    a section of the shank (6), in which the distal bend region (16, 30) is situated, is rotatable about a longitudinal axis relative to a section of the shank (6) in which the proximal bend region (10) is situated, and
    the jaw part (4) is rotatable relative to the shank (6) about its distal longitudinal axis at the distal end.

2. The medical instrument according to claim 1, wherein the shank (6) comprises an outer shank tube (14), and wherein the at least one distal bend region (16, 30) is defined by an angle or a bend in the outer shank tube (14).

3. The medical instrument according to claim 2, wherein the outer shank tube (14) is rotatable relative to a proximal section of the shank (6).

4. The medical instrument according to claim 2, wherein the shank (6) comprises a rigid outer tube (8) which borders the handle (3), extends only over a proximal section of the shank (6), peripherally surrounds the outer shank tube (14), and defines the at least one proximal bend region (10) by an angle or a bend in the outer tube (8).

5. The medical instrument according to claim 4, wherein the outer shank tube (14) is rotatable about its longitudinal axis relative to the outer tube (8).

6. The medical instrument according to claim 5, wherein the outer shank tube (14) is connected at a proximal end to a rotation device (24) in the handle (3).

7. The medical instrument according to claim 4, wherein the outer shank tube (14) in the proximal bend region (10) is flexible.

8. The medical instrument according to claim 4, wherein the outer shank tube (14) in the proximal bend region (10) is formed of several rigid tube sections (32) which are movably connected to one another.

9. The medical instrument according to claim 2, wherein the jaw part (4) is rotatably attached on the distal end of the outer shank tube (14) and a rotatable inner tube (34) is arranged in the outer shank tube (14), the rotatable inner tube being connected at its proximal end to a rotation device (22) in the handle (3), and being connected at its distal end to the jaw part (4) in a rotationally fixed manner.

10. The medical instrument according to claim 9, wherein the inner tube (34) at least in the bend regions (10, 16, 30) is designed to be flexible.

11. The medical instrument according to claim 9, wherein the inner tube (34) at least in the bend regions (10, 16, 30) is formed of several rigid tube sections (35) which are movably connected to one another.

12. The medical instrument according to claim 2, wherein the jaw part (4) is releasably connected to the outer shank tube (14).

13. The medical instrument according to claim 1, wherein an actuation rod (36) for actuating the jaw part (4) extends inside the shank (6) from the handle (3) to the jaw part (4).

14. The medical instrument according to claim 1, wherein the shank (6) is releasably connected to the handle (3).

15. The medical instrument according to claim 1, wherein the jaw part (4) is formed as a forceps or as a scissors.

16. The medical instrument according to claim 1, wherein the instrument (1) is designed as an HF-instrument with a shank (6) which is insulated to the outside.

17. The medical instrument according to claim 1, wherein the section of the shank (6), in which the distal bend region (16, 30) is situated, is rigid and the section of the shank (6), in which the proximal bend region (10) is situated, is rigid, and wherein the shank (6) is bent at a predefined angle at both the distal bend region (16, 30) and the proximal bend region (10) such that the predefined angles cannot be changed.

18. A medical instrument comprising:
    a handle (3) at a proximal end of the medical instrument;
    a movable jaw part (4) at a distal end of the medical instrument;
    an actuation rod (36) extending from the handle (3) to the movable jaw part (4); and
    a shank (6) extending from the handle (3) to the movable jaw part (4), the shank (6) including:
        at least one proximal bend region (10) and at least one distal bend region (16, 30) such that the shank (6) is angled at the at least one proximal bend region (10) and the at least one distal bend region (16, 30);
        an outer tube (8) having a proximal end connected to a distal end of the handle (3) and a distal end extending distally beyond the at least one proximal bend region (10);
        an outer shank tube (14) at least partially arranged inside the outer tube (8), the outer shank tube (14) extending distally beyond the distal end of the outer tube (8) and distally beyond at least one distal bend region (16, 30); and
        an inner tube (34) arranged inside of the outer shank tube (14), the actuation rod (36) extends through an inside of the inner tube (34), the inner tube (34) being flexible at least at the at least one proximal bend region (10) and the at least one distal bend region (16, 30).

19. The medical instrument according to claim 18, wherein the outer shank tube (14) is rotatable about a longitudinal axis with respect to the outer tube (8), and the inner tube (34) is rotatable about the longitudinal axis with respect to the outer shank tube (14).

20. The medical instrument according to claim 18, wherein the outer tube (8) is rigid along an entire length thereof, and wherein the outer shank tube (14) is rigid at the at least one distal bend region (16, 30) and the outer shank tube (14) is flexible at the at least one proximal bend region (10).

* * * * *